(12) United States Patent
Singer et al.

(10) Patent No.: US 10,345,570 B2
(45) Date of Patent: Jul. 9, 2019

(54) DEVICE FOR OPTICAL EXAMINATION OF A SPECIMEN, METHOD FOR EXAMINING A SPECIMEN AND METHOD FOR TRANSFERRING A DEVICE INTO AN OPERATION-READY STATE

(71) Applicant: Carl Zeiss Microscopy GmbH, Jena (DE)

(72) Inventors: Wolfgang Singer, Aalen (DE); Aksel Goehnermeier, Essingen-Lauterburg (DE); Guenter Rudolph, Jena (DE); Johannes Ruoff, Aalen (DE); Christian Dietrich, Jena (DE); Rong Dong, St. Ingbert-Hassel (DE)

(73) Assignee: Carl Zeiss Microscopy GmbH, Jena (DE)

( * ) Notice: Subject to any disclaimer, the term of this patent is extended or adjusted under 35 U.S.C. 154(b) by 211 days.

(21) Appl. No.: 15/337,156

(22) Filed: Oct. 28, 2016

(65) Prior Publication Data

US 2017/0123198 A1 May 4, 2017

(30) Foreign Application Priority Data

Oct. 30, 2015 (DE) .......................... 10 2015 118 641

(51) Int. Cl.
*G01N 21/03* (2006.01)
*G02B 21/02* (2006.01)
(Continued)

(52) U.S. Cl.
CPC ......... *G02B 21/28* (2013.01); *G01N 21/0332* (2013.01); *G02B 21/02* (2013.01);
(Continued)

(58) Field of Classification Search
CPC ..... G02B 21/00; G02B 21/0004; G02B 21/02; G02B 21/18; G02B 21/24; G02B 21/26;
(Continued)

(56) References Cited

U.S. PATENT DOCUMENTS

| 4,707,075 | A | * | 11/1987 | Fukushima | ............ | G02B 23/26 |
| | | | | | | 385/117 |
| 7,502,165 | B2 | | 3/2009 | Wehner et al. | | |

(Continued)

FOREIGN PATENT DOCUMENTS

| DE | 10 2005 051 386 A1 | 5/2007 |
| DE | 10 2006 034 534 A1 | 1/2008 |

(Continued)

OTHER PUBLICATIONS

German Application No. 10 2015 118 641.1, Search Report, dated Jun. 10, 2016, 2 pages.

*Primary Examiner* — Derek S. Chapel
*Assistant Examiner* — Adam W Booher
(74) *Attorney, Agent, or Firm* — LaBatt, LLC

(57) ABSTRACT

The invention relates to a device for optical examination of a specimen with a cryo-immersion objective, having a stative, to which the cryo-immersion objective is fixed, wherein the cryo-immersion objective has a plurality of optical components, in particular lenses, and wherein the cryo-immersion objective has an optical front component which is in contact during operation with a coolable immersion liquid, having a specimen carrier for a specimen to be examined, having means for providing a cooled immersion liquid between the optical front component and the specimen to be examined on or against the specimen carrier. The device is characterized in that insulating means are present for interrupting a heat transition between the stative and the optical front component. The invention also relates to a method for examining a specimen, wherein with a device (Continued)

according to the invention a plurality of microscopic images are recorded, wherein for each of the individual images a different offset between a main housing and a separate housing is set. Finally the invention relates to a method for transferring a device according to the invention into an operation-ready state, wherein the components, cooled in operation, of the cryo-immersion objective, in particular the optical front component, are cooled with a coolant, in particular with liquid nitrogen, wherein the immersion liquid is cooled with a coolant, in particular with liquid nitrogen, and wherein thereafter the cooled components of the cryo-immersion objective are brought into contact with the immersion liquid.

47 Claims, 9 Drawing Sheets

(51) Int. Cl.
    *G02B 21/18*     (2006.01)
    *G01B 21/26*     (2006.01)
    *G02B 21/28*     (2006.01)
    *G02B 21/33*     (2006.01)
    *G02B 21/36*     (2006.01)
    *G02B 21/26*     (2006.01)

(52) U.S. Cl.
    CPC ............. *G02B 21/18* (2013.01); *G02B 21/26* (2013.01); *G02B 21/33* (2013.01); *G02B 21/362* (2013.01); *G01N 2021/0335* (2013.01)

(58) Field of Classification Search
    CPC ........ G02B 21/28; G02B 21/33; G02B 21/36; G02B 21/362; G02N 21/0332; G01N 2021/0335; F17C 3/02; F17C 3/04; F17C 3/08; F17C 3/085
    See application file for complete search history.

(56) References Cited

U.S. PATENT DOCUMENTS

| | | |
|---|---|---|
| 7,852,554 B2 | 12/2010 | Le Gros et al. |
| 7,884,998 B2 * | 2/2011 | Armstrong ......... G02B 17/0812 359/366 |
| 2007/0291361 A1 * | 12/2007 | Lee ......................... G02B 7/028 359/512 |
| 2014/0248649 A1 * | 9/2014 | Mayer ..................... C12Q 1/02 435/29 |
| 2014/0347459 A1 * | 11/2014 | Greenfield ........... G02B 21/361 348/79 |
| 2015/0248002 A1 * | 9/2015 | Ingersoll ................ G02B 21/28 359/395 |

FOREIGN PATENT DOCUMENTS

| | | |
|---|---|---|
| DE | 10 2008 058 785 A1 | 5/2010 |
| DE | 10 2014 101 172 A1 | 7/2015 |

* cited by examiner

DEVICE FOR OPTICAL EXAMINATION OF A SPECIMEN, METHOD FOR EXAMINING A SPECIMEN AND METHOD FOR TRANSFERRING A DEVICE INTO AN OPERATION-READY STATE

The current application claims priority to German Application No. 102015118641.1, which was filed on 30 Oct. 2015, and which is hereby incorporated by reference.

The invention relates in a first aspect to a device for optical, in particular microscopic, examination of a specimen.

In further viewpoints the present invention relates to a method for examining a specimen using a device according to the invention and to a method for transferring a device according to the invention into an operation-ready state.

A generic device for optical examination of a specimen is disclosed in U.S. Pat. No. 7,852,554 and has firstly a cryo-immersion objective and a stative, to which the cryo-immersion objective is fixed, wherein the cryo-immersion objective has a plurality of optical components, in particular lenses, and wherein the cryo-immersion objective has an optical front component which is in contact with a coolable immersion liquid during operation. Finally, a generic device for optical examination of a specimen has a specimen carrier for a specimen to be examined and means for providing a cooled immersion liquid between the optical front component and the specimen to be examined on or against the specimen carrier.

The object of so-called "correlative microscopy", which is also described as multimodal microscopy, is to image microscopically small specimen points with different microscopy techniques and/or to superimpose in a defined manner the images obtained from one and the same specimen region with different microscopy techniques. For this, transfer systems are needed for transferring a specimen between microscope systems which are each specialised for different imaging methods. For example it is of interest to apply correlative or multimodal microscopy also to specimens which, after the production of appropriate sections, which are examined with electron-microscopic techniques, for example TEM, which are now to be light-microscopically examined too. In known transfer systems it is necessary to calibrate specimens and/or specimen holders upon each transfer between the individual microscope means. For this, expert knowledge is required in relation to the operation of the microscope, as images of reference markers generally have to be recorded.

It can be regarded as an object of the invention to indicate an optical device for examining a specimen which can be coupled in a particularly simple way to devices, with which further examination techniques, in particular microscopy techniques, are possible.

This object is achieved by the device having the features of: a cryo-immersion objective, a stative, to which the cryo-immersion objective is fixed, wherein the cryo-immersion objective has a plurality of optical components, and wherein the cryo-immersion objective has an optical front component which is in contact during operation with a coolable immersion liquid, a specimen carrier for a specimen to be examined, means for providing a cooled immersion liquid between the optical front component and the specimen to be examined on or against the specimen carrier, characterized in that insulating means are present for interrupting a heat transition between the stative and the optical front component.

In addition, a method for examining a specimen and a method for transferring a device into an operation-ready state are disclosed.

The device of the type indicated above is further developed according to the invention by insulating means being present to interrupt a heat transition between the stative and the optical front component.

Advantageous exemplary embodiments of the device according to the invention are explained in the following description, in particular in association with the dependent claims and the attached figures.

It can be regarded as a core idea of the present invention to separate the stative of the device so extensively from the cooled components necessary for cryo-microscopy that this stative can be adopted as such virtually unchanged from the prior art. With the optic design and the mechanical structure of the device according to the invention, cryo-microscopy can accordingly be realised on a quasi-commercial stative, with all the options and facilities in relation to contrasts and microscopy methods that are possible on such a system. With the device according to the invention, in particular cryo-microscopy can be carried out on an object at temperatures of less than $-140°$ C. According to the invention cryo-immersion is thereby used in order to achieve an improved resolution with respect to devices to date.

A significant advantage of the device according to the invention is additionally that a calibration of the system can be extensively omitted for the normal user. The user essentially only still needs to correctly insert the specimen, which is connected to a standard frame, with which a mechanical positioning and orientation of the specimen relative to a coordinate system, generally thus relative to the stative, are then carried out.

It is thus a core idea of the invention to use a cooled immersion liquid which is in contact with an optical front component of the cryo-immersion objective on the one hand and the specimen on the other hand, and through which the numerical aperture of the cryo-immersion objective and hence the resolution of the image are improved. Since according to the invention insulating means are present to interrupt the heat transition between the stative and the optical front component, a commercial stative can in principle be used, as an extensive thermal decoupling of the cooled optical components of the cryo-immersion objective from the stative is possible. By means of the cryo-immersion liquid accordingly the numerical aperture and as a result also the resolution and the collecting efficiency can be significantly improved. By providing an interface to a quasi-commercial system, a high flexibility in relation to different examination methods and contrast principles is additionally facilitated. Finally, a transition from a live observation of biological specimens to cryo-fixing under microscopy observation is possible in principle.

The term "optical examination of a specimen" is understood in the present case in particular as the microscopic examination of a specimen. The term "cryo-immersion objective" is used to describe a microscope objective which is designed for use with an immersion liquid and is additionally suited to be cooled. The term "cooling" is thereby to be understood in principle to be any lasting temperature reduction below room temperature. In particular, however, temperatures below the freezing point of water, in particular significantly below the freezing point of water, such as for example the boiling temperature of liquid nitrogen (approximately $-190°$ C.) are hereby considered. A "stative" describes a component which is static with respect to a laboratory environment, for example a table. A "specimen carrier" is a means, against which or on which a specimen to be examined is mounted, held and/or fixed. Means for providing a cooled immersion liquid are understood to be all technical means, with which a cooled immersion liquid is provided between the optical front component and the specimen to be examined on or against the specimen carrier. An "optical front component" within the scope of this description is the last component of the cryo-immersion objective in relation to the immersion liquid, thus the optical component of the cryo-immersion objective that is directly in contact with the coolable immersion liquid. The "insulating means" are to be understood to be all technical means present for heat insulation, i.e. to interrupt the heat conduction between the stative and the optical front component.

The insulating means of the invention are in particular suited and designed so that the heat conduction between the stative and the cooled optical front component can be interrupted in such a way that the stative is at room temperature. This facilitates a particularly simple usability of the device according to the invention.

A preferred exemplary embodiment of the device according to the invention is characterised in that the cryo-immersion objective has a housing and that at least a part of the insulating means is formed by a, in particular pipe-piece-like, heat-insulating housing portion of the housing. This heat-insulating housing portion can be formed in particular directly neighbouring fixing means or adjacent to fixing means, with which the cryo-immersion objective is fixed to the stative. The fixing means can for example be a screw connection. The heat-insulating housing portion can be produced for example from a heat-insulating ceramic or a heat-insulating plastic.

A further preferred exemplary embodiment of the device according to the invention is characterised, additionally or alternatively to the possible development described above, in that fixing means are present, with which the cryo-immersion objective is fixed to the stative, and the fixing means at the same time form at least a part of the insulating means. In this variant the fixing means accordingly have a dual function, namely having the functions of fixing and heat insulation. Compact structures of the cryo-immersion objective are hereby made possible.

In these two preferred exemplary embodiments accordingly the components that are thermally insulated relative to each other are rigidly connected to each other. In particular the heat-insulating housing parts used are produced from a rigid material, such as for example ceramic. Besides, the housing parts, upon which no requirements are placed with respect to heat insulation, can be produced from metal.

Optionally a means can also be present, with which or via which the cryo-immersion objective is fixed to the stative, is heated in order to guarantee that the stative is at room temperature. Optionally, for this purpose, a suitable temperature regulation with thermo-elements positioned at suitable points can be provided.

A further preferred exemplary embodiment of the device according to the invention is characterised, additionally or alternatively to the above-described possible developments, in that, as part of the insulating means in the cryo-immersion objective, pumping channels are formed for pumping down an insulating volume. By pumping away the insulation volumes the heat transition through convection can be clearly reduced. By using the measure of providing suitable pumping channels, the heat transition between the stative and the optical front component is thus particularly effectively interrupted. Optionally, through this measure the insulation requirements upon other components can also be reduced and therefore cost-savings made. Pumpable insulation volumes are formed particularly preferably between the optical front component and the optical component, following it, of the cryo-immersion objective.

A further preferred exemplary embodiment of the device according to the invention is characterised, additionally or alternatively to the above-described possible developments, in that the housing of the cryo-immersion objective is formed by an inner housing and an outer housing, wherein a part of the insulating means is formed by an intermediate space, in particular one which can be evacuated, between the inner housing and the outer housing. In principle the housing of the cryo-immersion objective can also be formed as a single-walled housing. Simple and cost-effective structures are thereby possible. In the variant with an inner housing and an outer housing, an intermediate space that is already heat-insulating in itself can be particularly simply provided.

A further preferred exemplary embodiment of the device according to the invention is characterised, additionally or alternatively to the above-described possible developments, in that the optical front component is held on the outer housing and the other optical components of the cryo-immersion objective are held on the inner housing. This measure allows, in a constructively simple way, a clear reduction in the heat transition between the optical front component and the further components of the cryo-immersion objective to be achieved. In a particularly preferred variant, a portion, in particular tubular, of the outer housing is formed from a heat-insulating material as a part of the insulating means.

A further preferred exemplary embodiment of the device according to the invention is characterised, additionally or alternatively to the above-described possible developments, in that the cryo-immersion objective is at least partially surrounded by a heat-insulating jacket as part of the insulating means. Through this measure it is possible for a further improvement to be achieved in relation to the interruption of the heat transition between the stative and the optical front component.

A further preferred exemplary embodiment of the device according to the invention is characterised, additionally or alternatively to the above-described possible developments, in that at least the optical front component of the cryo-immersion objective is accommodated in or on a separate housing, and the other optical components of the cryo-immersion objective are accommodated in or on a main housing. By accommodating the optical front component in a separate housing, the optical front component and thus the part of the cryo-immersion objective that comes into contact with the cooled immersion liquid is already very extensively decoupled from the other optical components of the cryo-immersion objective. The interruption of the heat transition between the optical front component and the stative can then be achieved particularly well.

A further preferred exemplary embodiment of the device according to the invention is characterised, additionally or alternatively to the above-described possible developments, in that as part of the insulating means a jacket, at least partial, in particular complete heat insulating, of the separate housing is provided. This technical measure can be realised in a technically simple way due to the separate accommodation of the optical front component in the separate housing. In addition the interruption of the heat transition between the optical front component and the stative can be achieved particularly effectively. Since the contribution of the convection to the heat conduction between the optical front component and the next following optical component of the cryo-immersion objective sensitively depends on the geometric distance between the optical front component and the next following optical component, it is preferable to select this distance to be as large as possible.

A great temperature difference between the optical front component, thus the location of the beam entry into the microscope objective on the side of the microscope objective facing towards a specimen, and the location of the beam exit from the microscope objective on the side facing away from the specimen, can be achieved more simply and more effectively if in any case somewhere within the microscope objective the distance between two optical components, in particular lenses, following each other in the direction of the beam exit is particularly great. The term "distance" is thereby to be understood to be the clear distance between the optical components, for example the lenses, thus the distance between the surfaces, facing towards each other, of these components, and not the distance between the optical planes possibly defined by these components. Such a comparatively great distance can then be used for measures of heat insulation. For example the volume lying between the components under observation can be evacuated.

It is advantageous for example if the distance between the optical front component and the inwardly following component, in particular the following lens, is particularly large.

In variants of the device according to the invention the distance between a first optical component, in particular the front component, and a second optical component of the microscope objective, in particular a lens, which directly follows the first component in the optical beam path of the microscope objective, is preferably greater than 2 mm, particularly preferably greater than 3 mm and particularly advantageously greater than 4 mm.

In variants, wherein some of the optical components of the microscope objective, in particular lenses, are accommodated in a main housing and the other or, in any case, further optical components of the microscope objective, in particular the front component, in a separate housing, these advantageous values apply to the distance between the outer-lying optical component in the separate housing and the outer-lying optical component in the main housing. The latter is the optical component which directly follows the outer-lying component in the separate housing in the optical path of the microscope objective.

A further preferred exemplary embodiment of the device according to the invention is thus characterised, additionally or alternatively to the above-described possible developments, in that a distance between an outer-lying optical component in the separate housing and an outer-lying optical component in the main housing is greater than 2 mm, preferably greater than 3 mm and particularly preferably greater than 4 mm. With these geometric data, a particularly good reduction of the convection can be achieved, wherein at the same time the optical requirements can be realised. To produce these findings, a plurality of systematic examinations and calculations of the respective optical systems were carried out by the applicant.

A further preferred exemplary embodiment of the device according to the invention is characterised, additionally or advantageously to the above-described possible developments, in that a means for flushing an intermediate space between the separate housing and the main housing with a dry gas, in particular nitrogen or dry air, is present. By conveying dry gases, in particular nitrogen or dry air, past the optical components of the cryo-immersion objective, misting and/or icing-over of these components at low temperatures can be effectively avoided.

A further preferred exemplary embodiment of the device according to the invention is characterised, additionally or alternatively to the above-described possible developments, in that a volume for receiving the specimen to be examined and for receiving immersion liquid is formed in the separate housing. With this technical measure the connection of the optical front component via the immersion liquid to the specimen to be examined can be particularly simply realised.

A further preferred exemplary embodiment of the device according to the invention is characterised, additionally or alternatively to the above-described possible developments, in that manipulation means for mechanical manipulation of the specimen to be examined within the separate housing are present on the separate housing. Through these manipulation means, a mobility of the specimen relative to the optical path of the cryo-immersion objective is provided. Larger areas of the specimen can in principle also be examined.

A further preferred exemplary embodiment of the device according to the invention is characterised, additionally or alternatively to the above-described possible developments, in that mechanical manipulation means for adjusting the separate housing relative to the main housing are present. Through this measure, an adjustment of the optical front component relative to the other components of the cryo-immersion objective is made possible.

A further preferred exemplary embodiment of the device according to the invention is characterised, additionally or alternatively to the above-described possible developments, in that, additionally or alternatively to the above-described possible developments, the optical front component and at least one further optical component of the cryo-immersion objective are arranged in or on the separate housing, and in that an intermediate space between the further optical components and the optical front component can be evacuated. Through this measure, greater distances can be achieved between the separate housing and the main housing, in which the further optical components of the cryo-immersion objective are accommodated, because additional refractive power is provided by the further optical component in or on the separate housing. As a result, the heat transition between the optical front component and the stative can be interrupted even more effectively.

Where reference is made within the scope of the present description to volumes being pumped down in order to thereby interrupt the heat conduction through convection, it is understood that the evacuating volumes are suitably sealed. For this, elastic seals and/or adhesives, in particular adhesives suitable for low temperatures, can be used.

A further preferred exemplary embodiment of the device according to the invention is characterised, additionally or alternatively to the above-described possible developments, in that optical front components, in particular being identical, are present on the separate housing on opposite sides. Through this feature, a separate housing is provided which can be used in principle with two cryo-immersion objectives and wherein, additionally, without rotating the housing, a cryo-immersion objective or, more specifically, the components of the cryo-immersion objective other than the optical front component, can be positioned both on one and also on the other, opposing side.

A further preferred exemplary embodiment of the device according to the invention is characterised, additionally or alternatively to the above-described possible developments, in that two, in particular identical, cryo-immersion objectives are present, which are orientated coaxially and counter relative to each other. In this variant a specimen can be examined in principle through reflected light and in transmitted light.

A further preferred exemplary embodiment of the device according to the invention is characterised, additionally or alternatively to the above-described possible developments, in that the optical front component is formed by a lens, in particular with a planar front side, by a front plate, by a mirror of a catadioptric optical system or a combination of these components. If the component attaching to the immersion liquid has a planar boundary surface, the numerical aperture does indeed not depend upon the refractive index of the immersion liquid. Nevertheless, the use of the immersion liquid leads to a clear reduction of chromatic aberrations. The boundary surfaces of the optical components have, in the way known in principle, highly polished surfaces. A front plate can be connected to an adjacent lens for example by "fusion bonding" or by "wringing". The front plate, which can also be described as a cover plate, can be made for example from $SiO_2$. The transition points between the optical components and the housing parts are preferably sealed with seals or adhesives, in particular adhesives suited for low temperatures.

A further preferred exemplary embodiment of the device according to the invention is characterised, additionally or alternatively to the above-described possible developments, in that the numerical aperture of the cryo-immersion objective is greater than 1. If the numerical aperture of the cryo-immersion objective is greater than 1, higher resolutions can be achieved and the collecting efficiency of the objective is improved overall.

A further preferred exemplary embodiment of the device according to the invention is characterised, additionally or alternatively to the above-described possible developments, in that the cryo-immersion objective has at least one optical component that can be adjusted in z direction, in particular at least one lens that can be adjusted in z direction. With such optical components, in particular lenses, that can be optically adjusted in z direction, thus in the direction of the optical axis, on the one hand the focussing can be changed relative to the specimen and on the other hand spherical aberrations can be compensated. For example, therefore, if a cryo-immersion objective is corrected to a certain colour, longitudinal chromatic aberrations for an adjacent wavelength can be compensated by slightly adjusting the optical component.

A further preferred exemplary embodiment of the device according to the invention is characterised, additionally or alternatively to the above-described possible developments, in that flow channels are formed in the cryo-immersion objective for flushing through with an inert gas, in particular dry air or nitrogen. By flushing with a dry inert gas, in particular with dry air or nitrogen, a misting or icing-over of the optical components used can be reliably prevented.

A further preferred exemplary embodiment of the device according to the invention is characterised, additionally or alternatively to the above-described possible developments, in that the cryo-immersion objective has a catadioptric optical system. Such catadioptric systems are characterised in that the chromatic aberrations are particularly low.

A further preferred exemplary embodiment of the device according to the invention is characterised, additionally or alternatively to the above-described possible developments, in that the cryo-immersion objective is sealed to prevent the penetration of immersion liquid. Through this measure, the misting or icing-over of optical components in the cryo-immersion objective is reliably prevented.

A further preferred exemplary embodiment of the device according to the invention is characterised, additionally or alternatively to the above-described possible developments, in that the means for providing the cooled immersion liquid have a container to receive the immersion liquid, wherein the cryo-immersion objective at least partially immerses into the immersion liquid during operation. This technical solution can be realised particularly simply. In particular the container with the cooled immersion liquid for its part can immerse into a container with a cooling liquid, in particular with liquid nitrogen. It is additionally particularly preferred that the specimen carrier is located during operation in a bath of immersion liquid, into which the cryo-immersion objective at least partially immerses. It is also particularly useful if mechanical manipulation means, in particular a lifting spindle, are present for mechanical manipulation of the specimen carrier within the bath of the immersion liquid. For example, with the aid of these mechanical manipulation means, the specimen carrier can be moved from the cryo-immersion objective of the device according to the invention to a further examination device, for example an electron microscope.

A further preferred exemplary embodiment of the device according to the invention is characterised, additionally or alternatively to the above-described possible further developments, in that a cover is present to prevent the escape of evaporating immersion liquid. By covering the immersion liquid, in particular turbulences, for example through boiling immersion liquid, can be prevented. Such turbulences can possibly lead to optical non-homogeneities and thus to the impairment of the measurement results.

A further preferred exemplary embodiment of the device according to the invention is characterised, additionally or alternatively to the above-described possible developments, in that the means for providing the immersion liquid are formed by a line for conveying immersion liquid between the optical front component and the specimen to be examined. For the realisation of the invention, it is in principle only a matter of the cooled immersion liquid being brought in some way between the optical front component and the specimen to be examined. Providing a line for this, with which a suitable amount of cooled immersion liquid can be introduced, constitutes a particularly simple and effective variant.

A further preferred exemplary embodiment of the device according to the invention is characterised, additionally or alternatively to the above-described possible developments, by means for cooling the immersion liquid to temperatures of less than 110 K (−163° C.) being present, in particular a bath with liquid nitrogen. If the immersion liquid for its part is itself cooled with the aid of a certain coolant, on the one hand lower temperatures than the respective boiling point temperature of the immersion liquid can be reached. The possibility of cooling in a bath with liquid nitrogen can be realised particularly cost-effectively In addition, a method for examining a specimen is claimed, wherein with a device according to the invention of the above-described type, wherein at least the optical front component of the cryo-immersion objective is accommodated in or on a separate housing, and the other optical components of the cryo-immersion objective are accommodated in or on a main housing, a plurality of microscopic images are recorded, wherein for the individual images a different offset between the main housing and the separate housing is set. With the aid of this method it is particularly simple to determine a correct positioning of the separate housing relative to the main housing. Once such a correct positioning has been found, i.e. if the optical axes of the optical front component in the separate housing and the optical axis of the further optical components in the main housing are orientated relative to each other, the specimen to be examined can be displaced in the separate housing with suitable manipulation means. All in all, using this method, a particularly good manageability and transferability of the specimens between individual microscopy methods is possible.

Finally a method is claimed for transferring a device according to the invention of the above-described type into an operation-ready state, wherein the components of the cryo-immersion objective cooled in operation, in particular the optical front component, are cooled with a coolant, in particular with liquid nitrogen, wherein the immersion liquid is cooled with a coolant, in particular with liquid nitrogen, and wherein thereafter the cooled components of the cryo-immersion objective are brought into contact with the immersion liquid. Through this method, boiling of the immersion liquid is reliably avoided. This factor has an advantageous effect on the stability of the whole system and an operation-ready state, in which a specimen can be examined, is facilitated in a very short time.

Further advantages and features will be described with respect to the drawings, in which.

The same and similar components are identified in the drawings as a rule with the same reference symbols.

Figure 1:
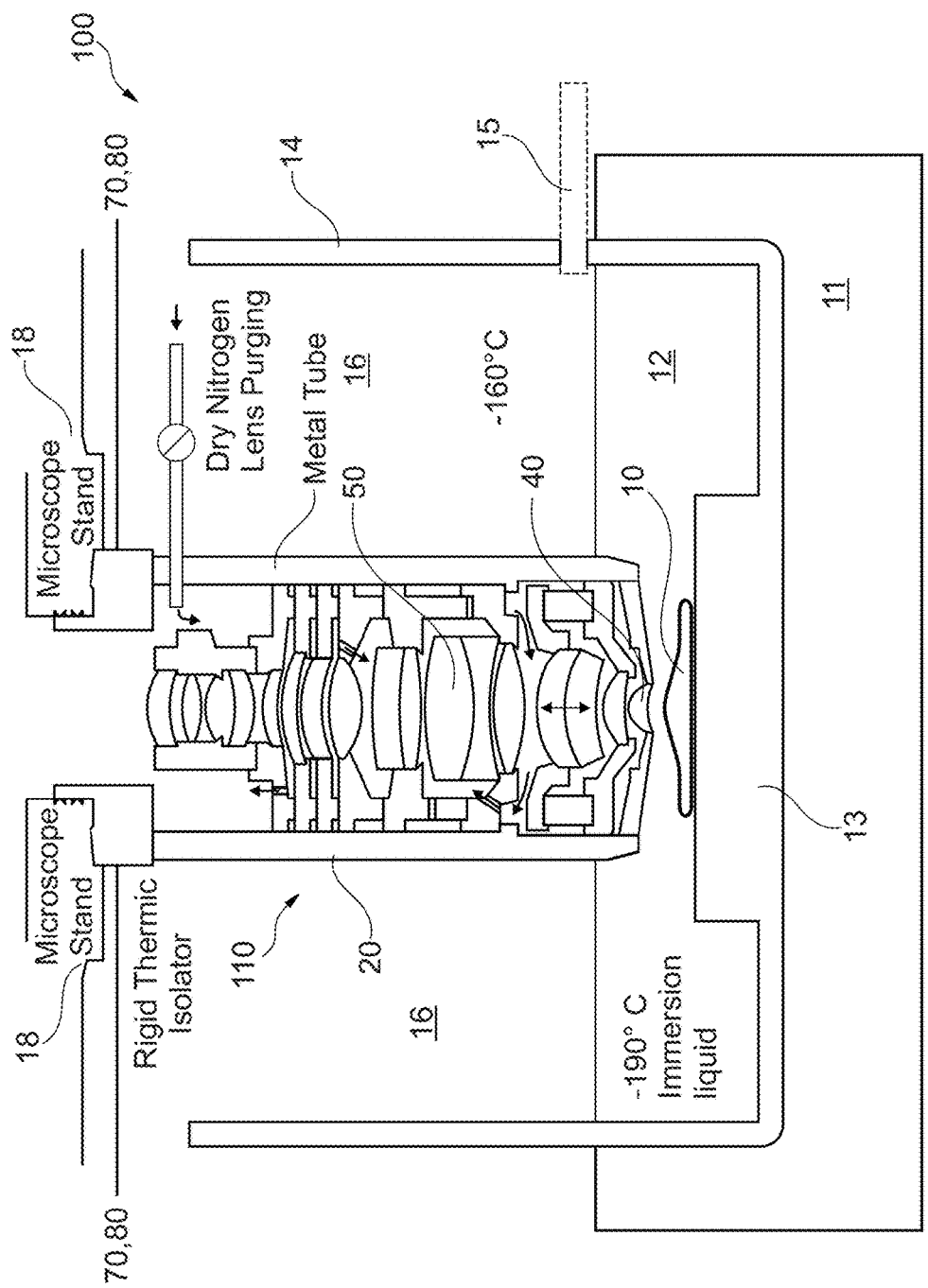
FIG. 1 shows a first exemplary embodiment of a device according to the invention.

A first exemplary embodiment of a device 100 according to the invention is explained by reference to FIG. 1. The device 100, shown therein, for optical examination of a specimen 10 firstly has a cryo-immersion objective 110 and a stative 18, to which the cryo-immersion objective 110 is fixed. The cryo-immersion objective 110 has a plurality of optical components, of which for example one lens 50 is indicated, and in addition an optical front component 40, which is in contact during operation with a coolable immersion liquid 12. Furthermore a specimen carrier 13, a specimen table 13 in the example schematically shown in FIG. 1, is present for a specimen 10 to be examined. Finally, means 14 for providing the cooled immersion liquid 12 between the optical front component 40 and the specimen 10 to be examined are present on or against the specimen carriers 13.

In the situation shown in FIG. 1, the means for providing the immersion liquid are formed by a container 14, in which the respectively used immersion liquid, for example ethane, butane, pentane and so on (see in this connection for example U.S. Pat. No. 7,862,554), is contained. In the container 14 a feed line 15 is formed, via which cold nitrogen 16 can be introduced into the container. In this way, the evaporation of immersion liquid can be prevented. This cold nitrogen supply 16 generally has a temperature lying above the boiling temperature of liquid nitrogen, for example this temperature can be approximately −160° C. The container 14 for its part immerses into a bath of liquid nitrogen 11 and is thereby cooled to the boiling temperature of liquid nitrogen, i.e. to approximately −190° C. As can be seen from FIG. 1, the specimen carrier 13 with the specimen 10 located thereon is located completely in the immersion liquid 12 and the cryo-immersion objective 110 immerses partially into the supply of the immersion liquid 12, i.e. the intermediate space between the optical front component 40 and the specimen 10 to be examined is completely filled by immersion liquid 12.

The cryo-immersion objective 110 has a housing 20, in which the optical components are accommodated. In this housing 20, as indicated in FIG. 1 by a plurality of arrows, a plurality of flow channels are formed, through which during operation a dry flushing gas, for example nitrogen or dry air, can be passed. In this way, misting or icing-over of the optical components of the cryo-immersion objective 110 can be reliably prevented. To introduce the flushing gas, an inlet 22, which can be closed with a valve, is present. In addition the housing 20 is suitably sealed in order, in particular in the area of the optical front component 40, with which the cryo-immersion objective 110 immerses into the supply of the immersion liquid 12, to prevent immersion liquid 12 entering the cryo-immersion objective.

An essential component of the exemplary embodiment shown in FIG. 1, finally, is an insulating means 70, which in the example of FIG. 1 is formed as a heat-insulating, pipe-piece-like housing portion. This housing portion is additionally formed as a screw element, with which the cryo-immersion objective can be screwed into the stative and thereby fixed to the stative 18. This screw connection 80, which serves in the example of FIG. 1 as insulating means, can preferably be formed from a heat-insulating ceramic. Through this heat-insulating screw connection it is ensured that in measurement operation the stative 18 is practically at room temperature, whereas the optical front component 40 of the cryo-immersion objective is at the boiling temperature of liquid nitrogen, thus at approximately −190° C. With this exemplary embodiment the coupling of immersion microscopy for frozen specimens (cryo-immersion microscopy) to a conventional stative is facilitated.

A second exemplary embodiment of a device 200 according to the invention will now be described by reference to FIG. 2. The device 200 shown there for optically examining a specimen 10 has in turn a cryo-immersion objective 210, which is fixed to a stative 18, and contains a plurality of optical components, in particular lenses 50. In addition the cryo-immersion objective 210 has an optical front component which is formed in FIG. 2 by a lens 40 and a front plate 41. The specimen 10 to be examined is again located on a specimen table 13 which is completely surrounded in the situation shown in FIG. 2 by a cooled immersion liquid 12. The specimen table 13 with the specimen 10 is located together with the immersion liquid 12 in a container 14, through which the means present according to the invention for providing a cooled immersion liquid 12 between the optical front component 40, 41 and the specimen 10 to be examined are formed on or against the specimen carrier 13. With regard to the cooling of the immersion liquid 12 in the container 14, the exemplary embodiment shown in FIG. 2 corresponds to the variant of FIG. 1.

Figure 2:
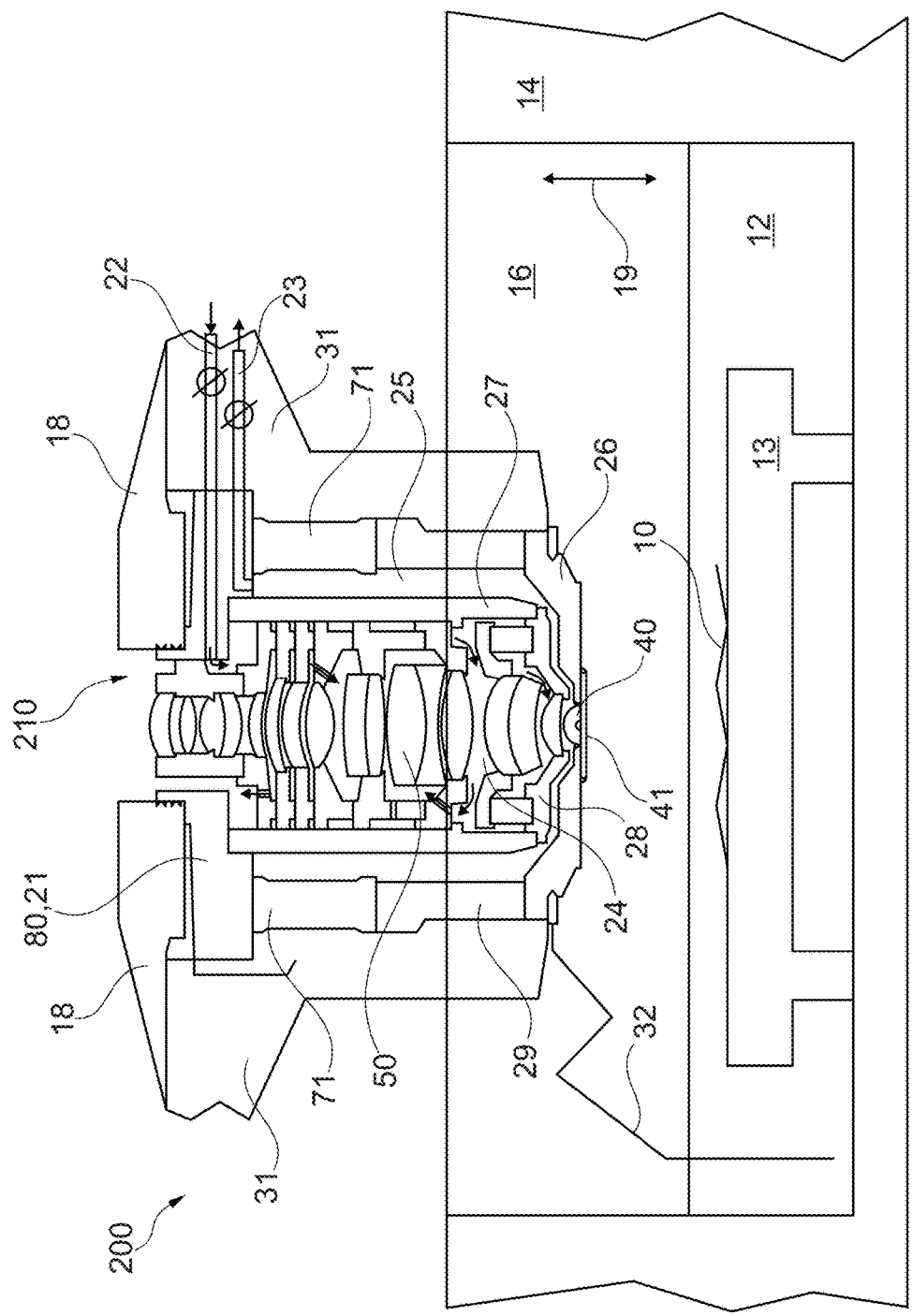
FIG. 2 shows a further exemplary embodiment of a device according to the invention.

Unlike the example of FIG. 1, the cryo-immersion objective 210 of FIG. 2 has an inner housing, which is formed substantially by an inner housing pipe 27 and a front-side closure 28 of this inner housing pipe 27. Furthermore an outer housing is present which is formed by a heat-insulating housing portion 71, which can be produced for example from a heat-insulating ceramic, a pipe piece 29 and a front-side closure element 26 of the pipe piece 29. The optical front component 40, 41 is held on the front-side closure element 26, whereas all other optical components 50 of the cryo-immersion objective 210 are held on the inner housing, i.e. on the inner housing pipe 27 or the front-side closure 28 of the inner housing pipe 27. An insulating volume 25 is formed between the inner housing pipe 27, 28 and the outer housing pipe 71, 29, 26, which insulating volume 25 is evacuated during operation via a line 23, thus pumped away. For this, the cross-sections within the cryo-immersion objective 210, thus the fluid conductances, are suitably formed. For example, already by lowering the pressure by a factor of 1000 to approximately 1 mbar, a good heat insulation is achieved between the inner housing 27, 28 and the outer housing 71, 29, 26. In the inner housing in addition, as in the exemplary embodiment of FIG. 1, flow channels 24 are formed in order to flush out the optical components 50 contained there via the feed line 22 with a dry flushing gas, for example dry nitrogen or dry air. In this way, as described in association with FIG. 1, the misting or icing-over of the optical components can be reliably prevented.

In the situation shown in FIG. 2, the cryo-immersion objective 210 does not immerse into the immersion liquid 12, but instead is located in the cold nitrogen supply 16. For the measurement operation the cryo-immersion objective 210 and the specimen table 13 must be moved towards each other along the direction of the double arrow 19 until at least the optical front component 40, 41 of the cryo-immersion objective 210 immerses into the immersion liquid 12. The specimen table can in this exemplary embodiment, as is also the case generally for the device according to the invention and also in the other exemplary embodiments, be a specimen table, with which a movement of the specimen 10 to be examined in the three coordinate directions X, Y and Z is possible. To cool the front-side closure element 26 of the outer housing of the cryo-immersion objective 210 and thus also the optical front component 41, 40, in the exemplary embodiment of FIG. 2 a heat bridge 32 is additionally present. This can in principle be a wire which is thermally coupled to the cold immersion liquid 12. It is hereby possible to prevent the cryo-immersion objective being too greatly heated if it is removed from the supply of the immersion liquid 12. An evaporation of immersion liquid 12 when re-immersing the cryo-immersion objective 210 into the immersion liquid 12 can thereby be avoided or at least reduced.

As insulating means for interrupting the heat transition between the optical front component 40, 41 and the stative 18, a heat-insulating housing portion 71 is present in the exemplary embodiment in FIG. 2, wherein it can be a pipe piece produced for example from heat-insulating ceramic. By way of deviation from the example of FIG. 1, however, in FIG. 2 it is a pipe portion which is formed to be significantly longer in the direction of the optical axis of the cryo-immersion objective 210, whereby the insulating properties can be improved. The housing portion 71 attaches to a screw connection 80 which serves as fixing means 80 between the cryo-immersion objective 210 and the stative 18. In the connecting piece 21, the feed lines 22, 23 for introducing a flushing gas or for evacuating the insulating volumes 25 are formed. The whole cryo-immersion objective 210 is surrounded with a heat-insulating jacket 31, for example made of polystyrene, which also serves as insulating means for interrupting the heat transition between the stative 18 and the optical front component 40, 41. All in all, also with the exemplary embodiment shown in FIG. 2 an operating situation is achieved, wherein the stative 18 is essentially at room temperature and the optical front component 40, 41 is at the temperature of the cold (for example −190° C.) immersion liquid.

Figure 3:
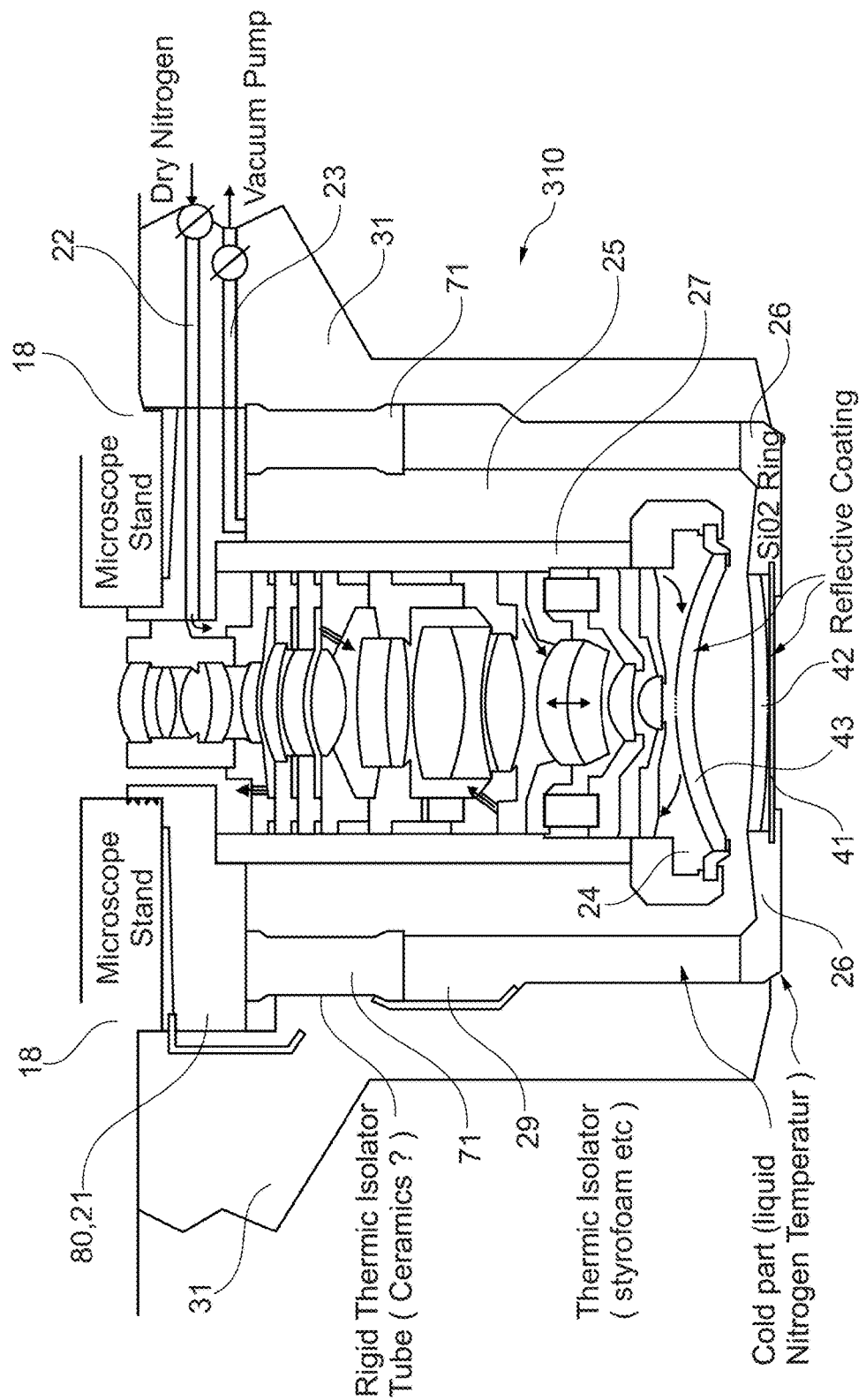
FIG. 3 shows an exemplary embodiment of a cryo-immersion objective for a device according to the invention.

The exemplary embodiment, shown in FIG. 3, of a cryo-immersion objective 310 is a variant of the cryo-immersion objective 210 shown in FIG. 2. The differences lie in the region of the optical front component. The cryo-immersion objective 310 has a catadioptric optical system which is formed by a first hollow mirror 42 and a second hollow mirror 43. The first hollow mirror 42 and the second hollow mirror 43 each have a reflective coating which is only interrupted in a circular disc shaped window formed symmetrically to the optical axis. The first hollow mirror 42 is connected to a front plate 41 which comes into contact during operation with the immersion liquid 12. Light entering through the window formed in the hollow mirror 42 is reflected by the reflective coating of the second hollow mirror 43 onto the coating of the first hollow mirror 42 and by this is directed through the window in the second hollow mirror 43 to the further optical components of the cryo-immersion objective 310. The first hollow mirror 42 is held on the outer housing 71, 29, 26, whereas the second, inner hollow mirror 43 of the cryo-immersion objective 310 is held on the inner housing 27. In all other viewpoints, in particular as regards the insulating means according to the invention for interrupting the heat transition between the stative 18 and the optical front component 41, 42, the exemplary embodiment shown in FIG. 3 corresponds to that of FIG. 2. The first and the second hollow mirrors can be for example a Mangin mirror, i.e. lenses, of which the rear side is mirrored at least in part.

Figure 4:
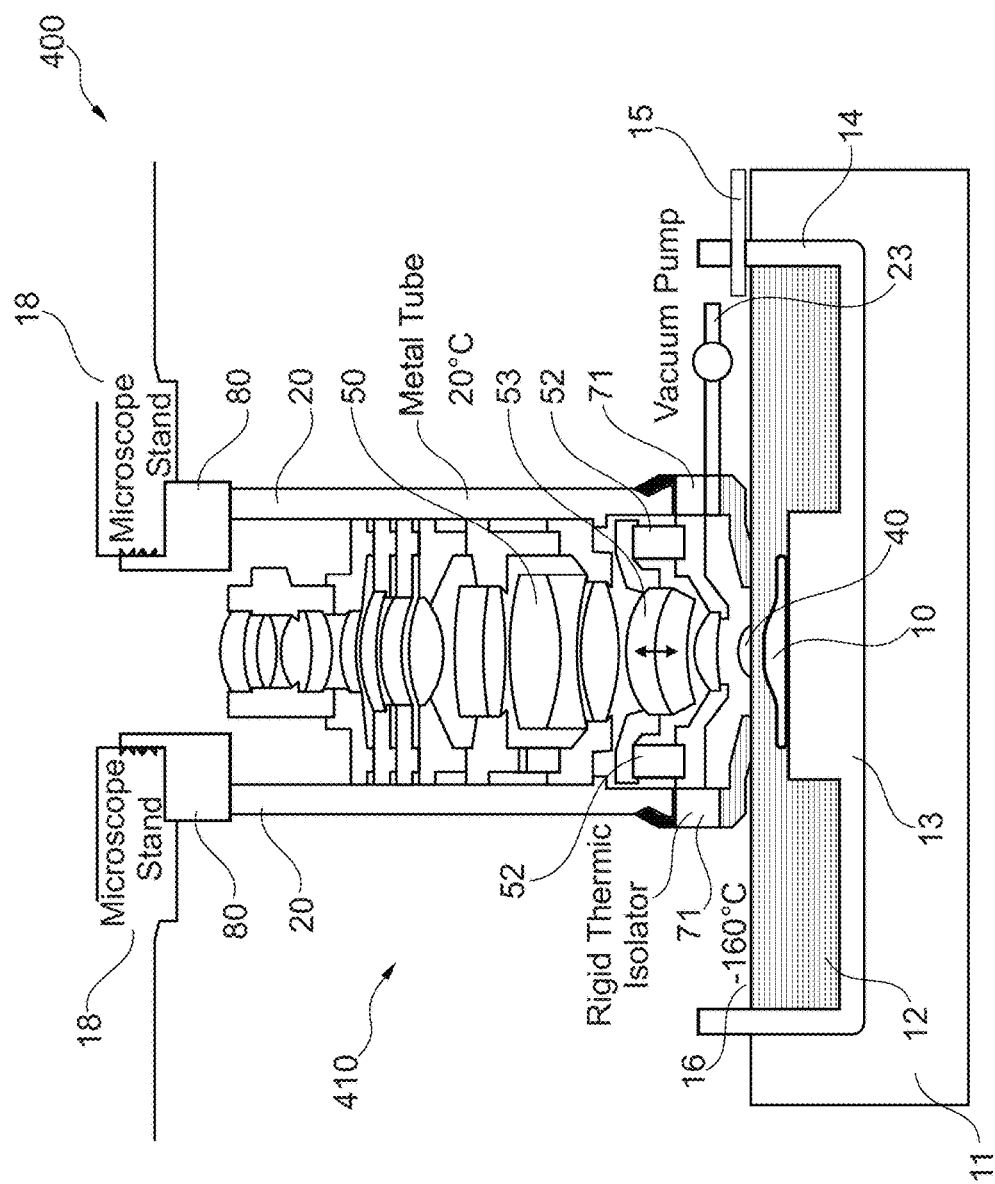
FIGS. 4 to 9 show further exemplary embodiments of devices according to the invention.

A further variant of a device according to the invention with a cryo-immersion objective 410 is shown in FIG. 4. The essential difference of this exemplary embodiment in comparison with the variants explained thus far is that the insulating means for interrupting the heat transition between the stative 18 and the optical front component 40 are formed by a heat-insulating housing portion which is formed in a front region of the cryo-immersion objective 410. This means that the heat transition is already interrupted shortly after the optical front component 40. In this way it can be ensured particularly reliably that the stative 18 during operation is essentially at room temperature. As in the examples of FIGS. 2 and 3, in the variant in FIG. 4 an intermediate space between the optical front component 40 and the next following optical component of the cryo-immersion objective 410 can be pumped out via an attachment 23 for a vacuum pump. With regard to the cooling of the immersion liquid 12, the cold nitrogen supply 16 located above it and the cooling of the immersion liquid 12 with liquid nitrogen 11, the example of FIG. 4 corresponds to that of FIG. 1. It is additionally shown in the variant of FIG. 4 that the cryo-immersion objective 410 has a lens 53 that is adjustable in the direction of the optical axis, thus in the z direction. The adjustment in the direction of the optical axis is thereby managed with piezo-actuators 52. Through this adjustment, on the one hand, spherical aberrations can be compensated and on the other hand the focus plane can be adjusted within a specimen, in any case within certain boundaries.

Figure 5:
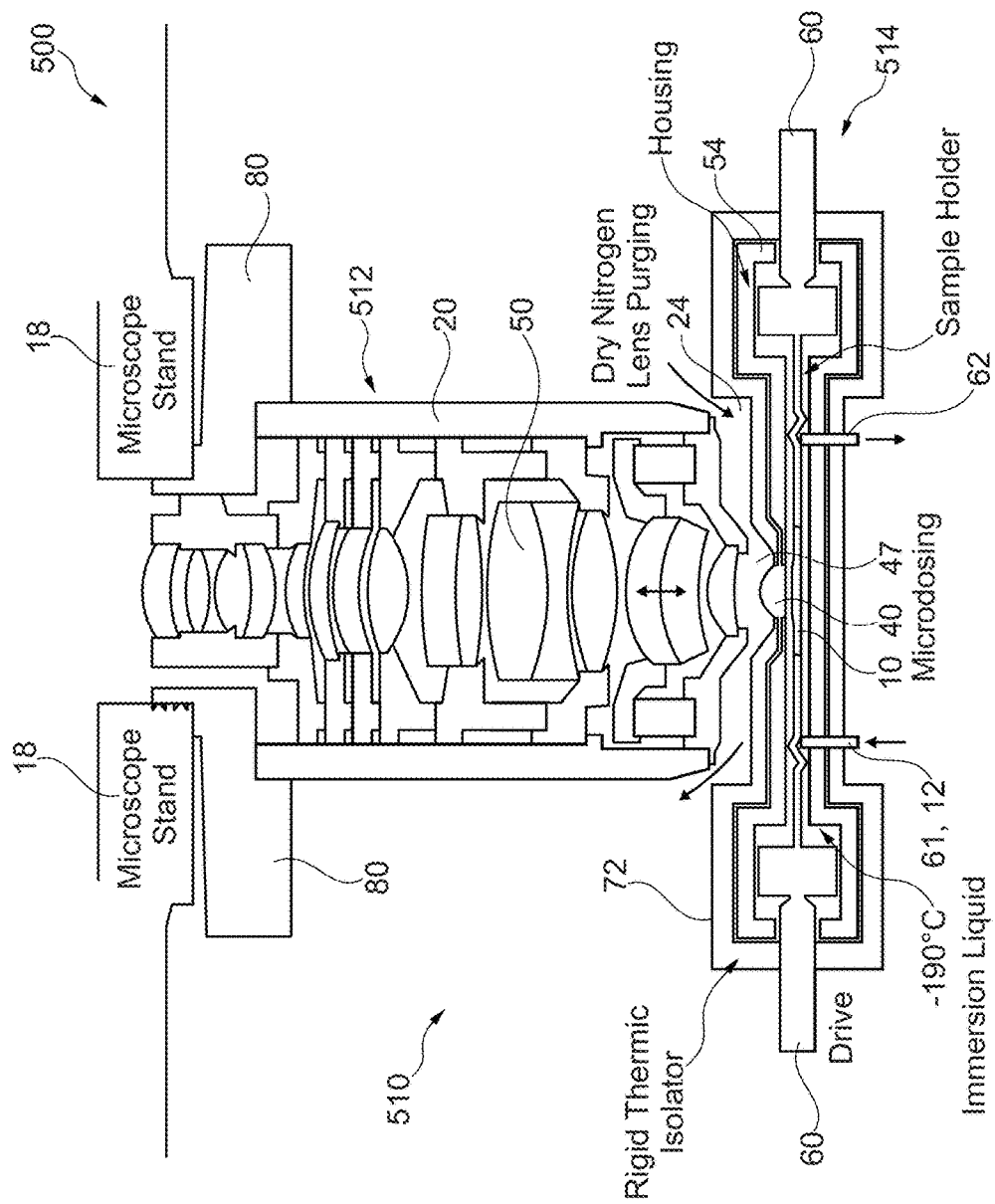

A fundamentally different variant of a device 500 according to the invention is described with reference to FIG. 5. The essential difference of this exemplary embodiment in comparison with the variants discussed thus far is that the optical components of the cryo-immersion objective 510 are no longer located in one and the same housing, but instead are divided across two different housings. The optical front component 40 is held in a separate housing 514 and the other optical components, for example identified by reference numeral 50, are located in a main housing 512, which essentially consists of the housing 20 which is connected via a screw connection 80 as fixing means to the stative 18. The essential advantage of the exemplary embodiment of FIG. 5 is that the main housing 512 is already very extensively thermally decoupled from the cooled components, thus the optical front component 40. An intermediate space 47 between the outer-lying optical component of the main housing 512 and the outer-lying optical component of the separate housing 514, the optical front component 40 itself in the example shown in FIG. 5, can in turn be flushed to prevent the misting or icing-over in operation with a dry flushing gas, for example nitrogen or dry air. For this, suitable flow channels 24 are provided. The separate housing 514 as such consists of the actual, inner housing 54, which for its part is surrounded by an insulating housing 72 which can be formed for example from ceramic. Within this housing 54, the specimen 10 to be examined is arranged, which can be manipulated with the aid of mechanical manipulation means 60 within the separate housing 514, i.e. can be moved back and forth. In addition an inlet 61 and an outlet 62 for immersion liquid are present in the separate housing 514. The mechanical manipulation means 60 can for example be suitable threaded spindles, with which the specimen 10 can be moved relative to the separate housing 514. Particularly preferably, in addition, further (not shown) mechanical manipulation means are present, with which the separate housing 514 can be positioned in a defined way relative to the main housing 512. This is necessary for example in order to orientate the optical axes of the optical front component 40 relative to the optical axis of the further optical component 50.

Figure 6:
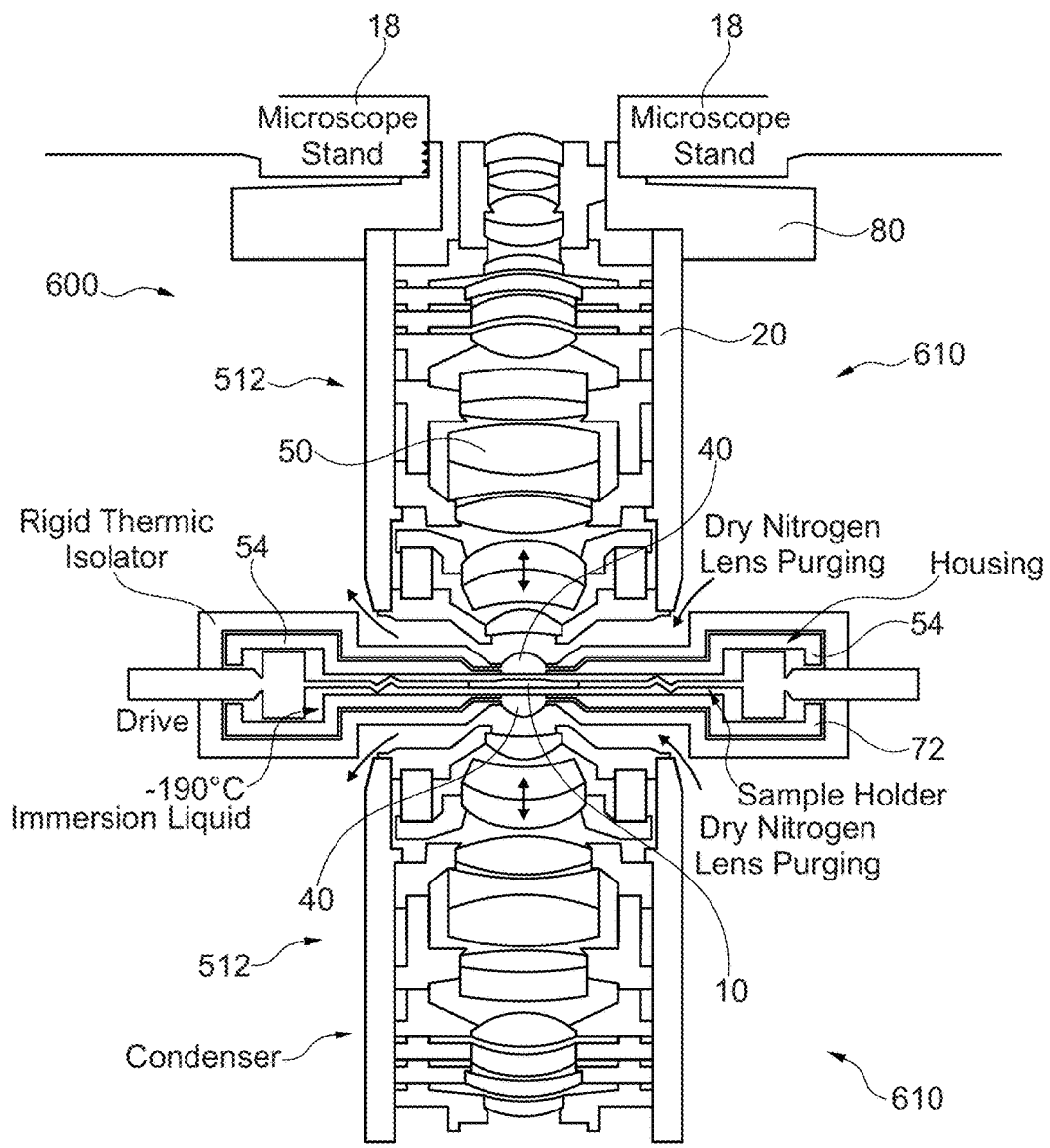

The exemplary embodiment shown in FIG. 6 is a further development of the variant of FIG. 5. It is thereby essential that two, in the present case identical, cryo-immersion objectives 610 lying opposite each other are present, each provided with an identical main housing 512 which corresponds essentially to the main housing 512 of FIG. 5.

The device 600 according to the invention of FIG. 6 has differences in comparison with FIG. 5 in the region of the separate housing 516. Unlike the variant of FIG. 5, in the main housing 516 of FIG. 6 optical front components 40 are present on both sides which in particular can be identical. The specimen 10 to be examined, which, as in the variant of FIG. 5, is surrounded by immersion liquid is located between these optical front components 40, so that, in the same way as in FIG. 5, only immersion liquid 12 is located between the optical front component 40 and the specimen 10. With the device 600 according to the invention of FIG. 6, the specimen 10 can be examined both in reflected light and also in transmitted light. As in FIG. 5, the heat-insulating jacket 72 of the inner housing 54 serves as insulating means for interrupting the heat transition between the optical front component 40 or the optical front components 40 and the stative 18. For the main housing 510, pointing downwards in FIG. 6, of the cryo-immersion objective 610, the stative itself is not shown.

Figure 7:
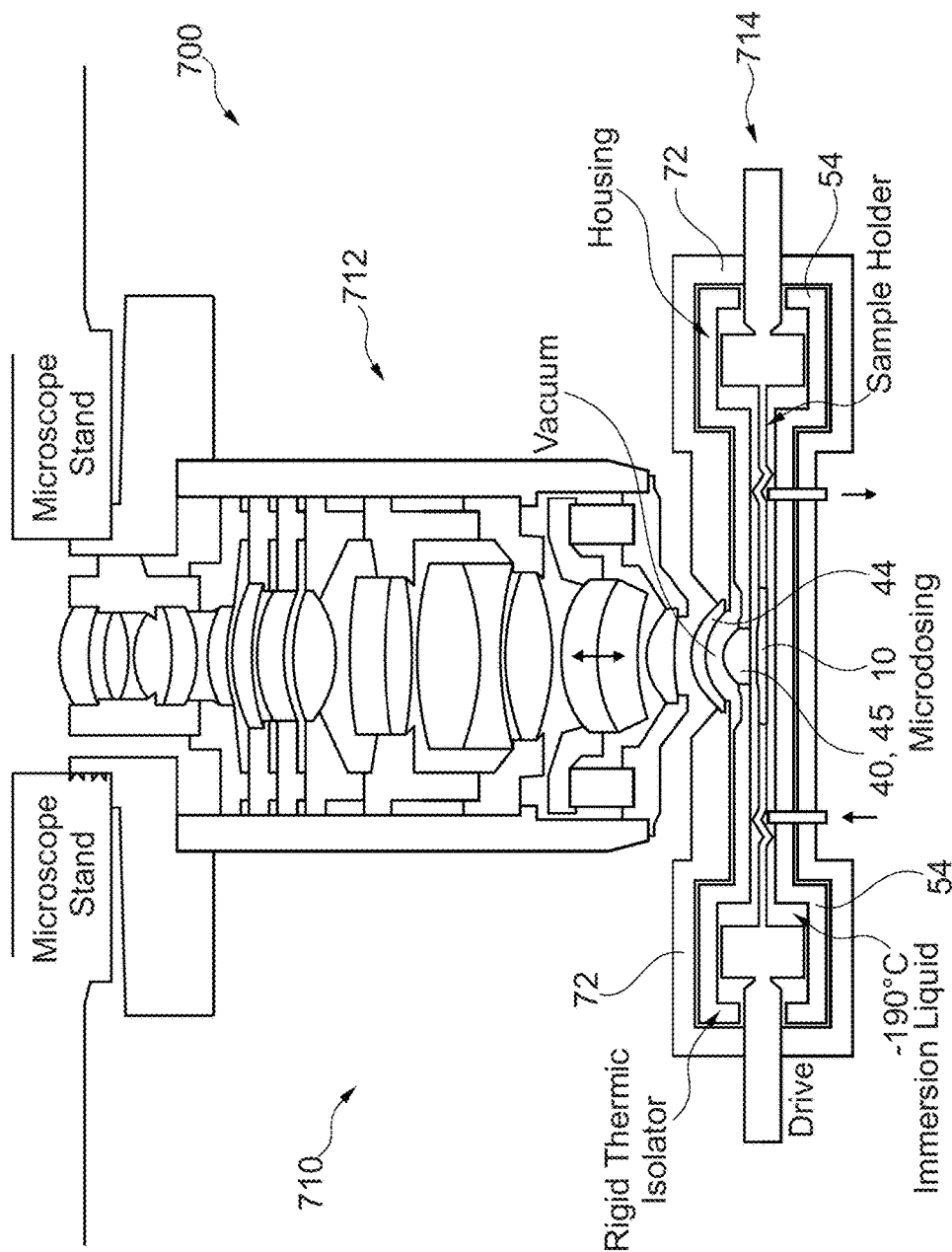

A further variant of a device 700 according to the invention for optical examination of a specimen is shown in FIG. 7. In turn, a cryo-immersion objective 710 is divided into optical components in a main housing 712 and optical components in a separate housing 714 which can be surrounded with an insulating jacket 72, in particular made of ceramic. The essential difference in the comparison with the variant shown in FIG. 5 is that in the main housing 714 in FIG. 7 not only the optical front component 40 formed by a lens 45 but also a further optical component 44, a lens in the example of FIG. 7, is held on the separate housing 714. More specifically, the further optical component 44 is held on the insulating jacket 72 whereas the optical front component 40, 45 is held on the inner housing 54, which forms the actual separate housing. An intermediate space between the further optical component 44 and the optical front component 40, 45 can be evacuated to further reduce the heat transition. With regard to the manipulation possibilities of the specimen 10 to be examined and the separate housing 714 relative to the main housing 712 and also with regard to the supply and removal of immersion liquid from and into the separate housing 714, the variant of FIG. 7 corresponds to those of FIGS. 5 and 6.

Figure 8:
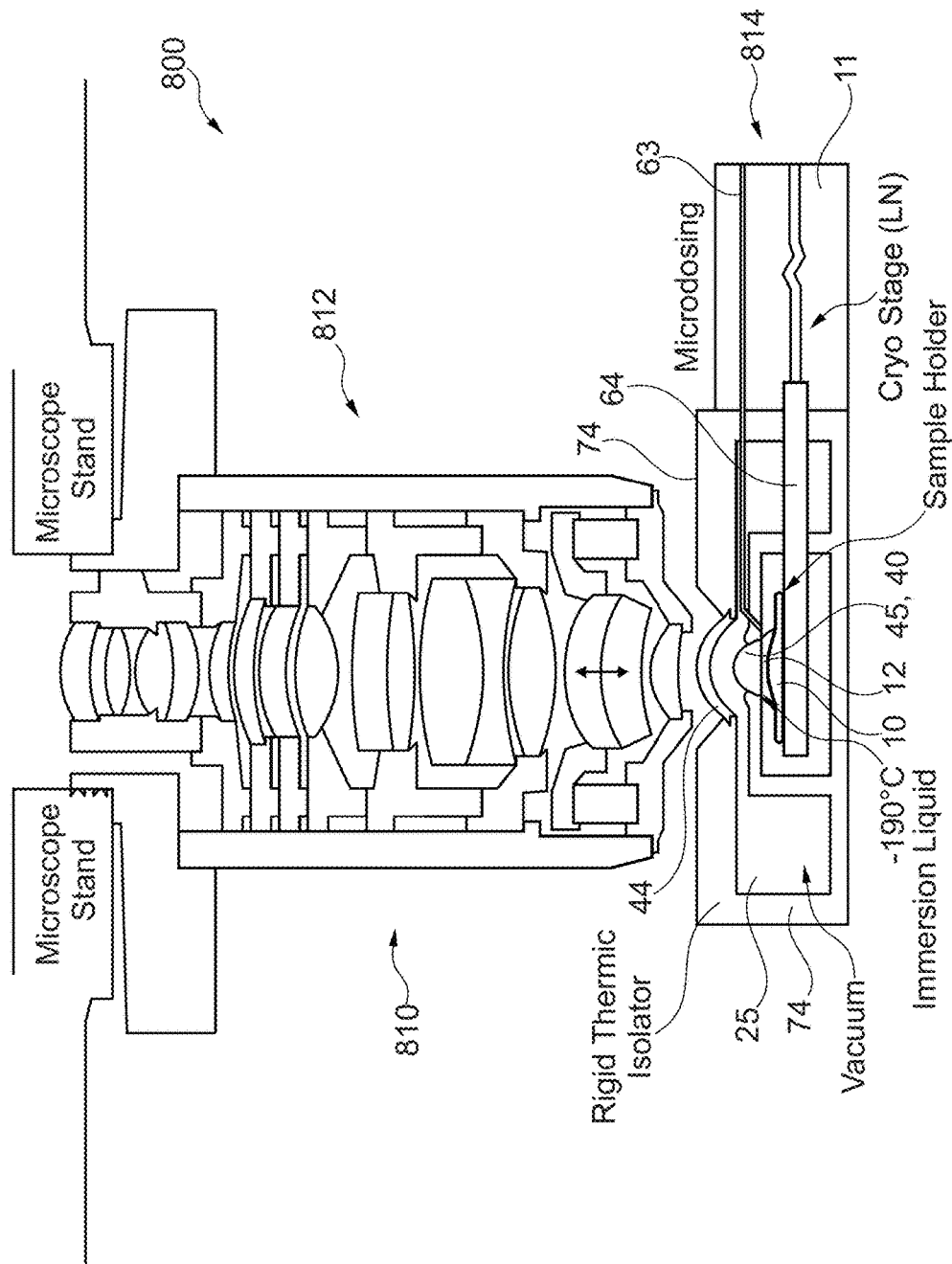

A further variation of the exemplary embodiment of FIG. 5 is shown in FIG. 8. The device 800 according to the invention shown therein for optical examination of a specimen has in turn a cryo-immersion objective 810 which is divided into a main housing 812 and a separate housing 814. The example of FIG. 8 has similarities to the variant of FIG. 7 insofar as also in FIG. 8 not only the optical front component 40, 45 itself is accommodated in the separate housing 814, but instead also a further optical component 44, namely a lens. The separate housing 814, by way of deviation from the variants of FIGS. 5 to 7, does not have an inner housing but instead is formed as such by a housing 74 that is already heat-insulating in itself, for example being made of ceramic. As can be seen from FIG. 8, the optical front component 40, 45 is held on an inner housing part and the further optical component 44 on an outer housing part of the housing 74. An intermediate space 25 between the further optical component 44 and the optical front component 40, 45 can thereby be evacuated for further reduction of the heat transition between the optical front component 40, 45 and the further optical component 44.

As means for providing the cooled immersion liquid 12, in the variant shown in FIG. 8 a feed line for immersion liquid 63 is present, with which the immersion liquid 12 is brought between the specimen 10 to be examined and the optical front component 40, 45. The specimen 10 to be examined is located on a cooled specimen holder 64, which is thermally coupled to a tank of liquid nitrogen 11. With the embodiment of FIG. 8, it can also be ensured in an excellent manner that the stative 18 during operation remains essentially at room temperature, whereas the specimen and the optical front component 40, 45 are at the temperature of liquid nitrogen, thus at approximately −190° C. The feed line 63 for the immersion liquid 12 is thereby also in a tank of liquid nitrogen 11.

Figure 9:
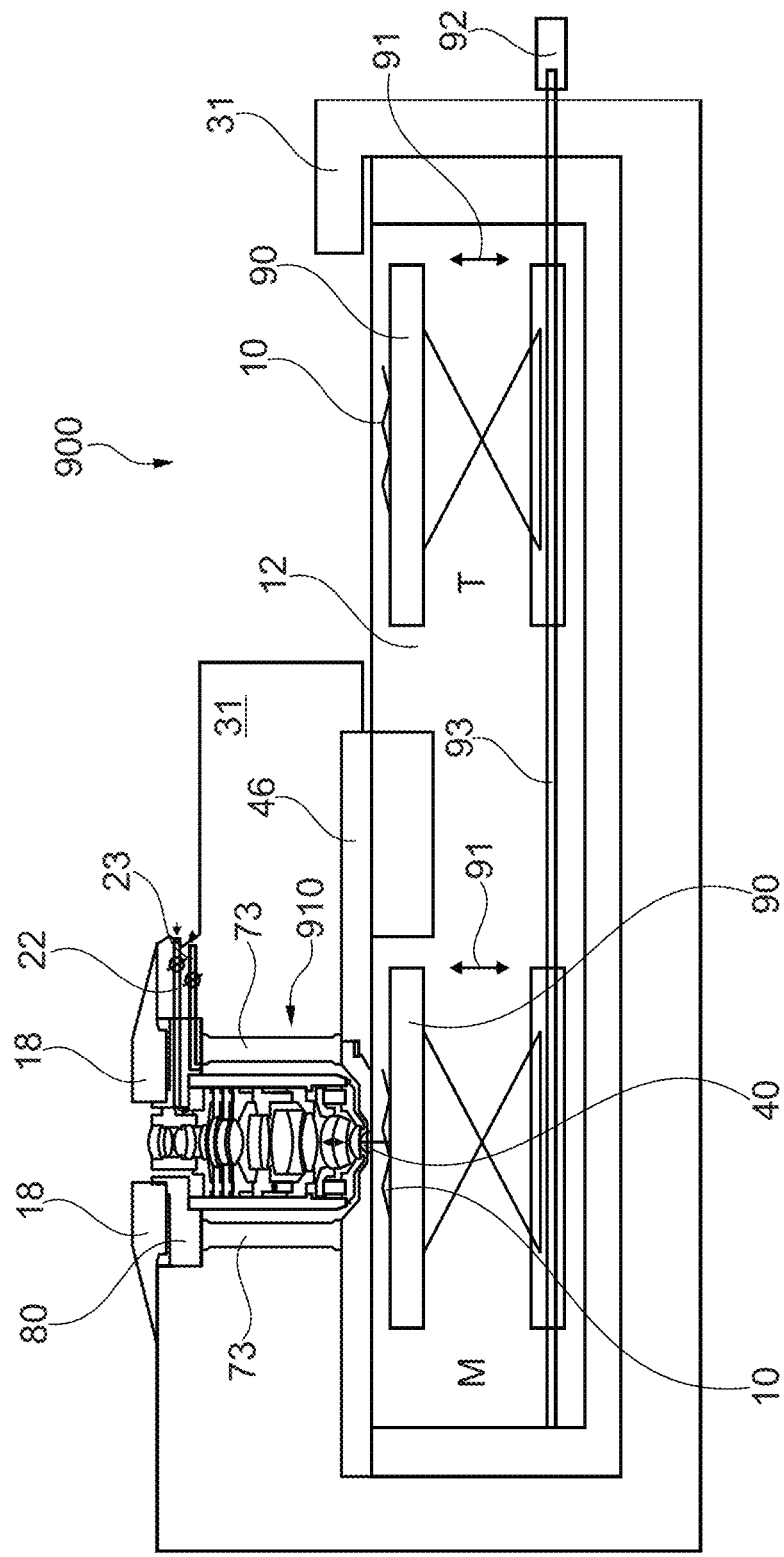

A further variant of a device 900 according to the invention for optical examination of a specimen is described, finally, in FIG. 9. With regard to the insulating means for interrupting the heat transition between the stative 18 and the optical front component, the variant of FIG. 9 has similarities to the exemplary embodiments described in connection with FIGS. 2, 3 and 4. Unlike the variant of FIG. 2, however, in FIG. 9 the outer housing of the cryo-immersion objective 910 is formed practically completely by a heat-insulating housing pipe 73, which extends between a screw connection 80, with which the cryo-immersion objective 910 is fixed to the stative 18, and a cover 46, on which the optical front component 40 is held. The cover 46 is a large plate, for example made of quartz glass, which lies during operation directly on the immersion liquid 12.

The specimen 10 to be examined is located in FIG. 9 on a specimen lifting table 90 which is shown in FIG. 9 both in a measurement or working position M below the cryo-immersion objective 910 and also in a transfer position T. With the double arrow 91, a degree of mobility of the specimen lifting table 90 in the vertical direction is indicated. The specimen lifting table 90 can be moved between the measurement or working position M below the cryo-immersion objective 910 and the transfer position T with the aid of mechanical manipulation means, concretely with a threaded spindle 93 and a drive 92, back and forth. Both in the measurement or work position M below the cryo-immersion objective 910 and also in the transfer position T, the specimen lifting table 90 is located completely in the cold immersion liquid which, as in the example described in association with FIG. 1, can be cooled via a bath of liquid nitrogen. From the transfer position T, the specimen 10 to be examined can be fed for further microscopy techniques, in particular electron microscopy, TEM. The whole tank for the immersion liquid 12 and the cryo-immersion objective 910 itself is surrounded in the situation shown in FIG. 9 with a heat-insulating jacket 31, which can be formed for example from polystyrene. With regard to the passing of a dry flushing gas through the optical components of the cryo-immersion objective 910 via an inlet 22 and with regard to the pumping away of insulating volumes via a pumping channel 23, the cryo-immersion objective 910 of FIG. 1 corresponds to the variant described in association with FIG. 2. It is significant in the example of FIG. 9 that the outer housing of the cryo-immersion objective 910 is produced practically completely from the heat-insulating pipe 73, for example from ceramic, and that the optical front component 40 directly contacts with the cover or closure plate 46, for example made of quartz, which comes completely into contact with the cold immersion liquid 12 and covers a large area of the liquid surface of the immersion liquid 12. This area corresponds to a multiple, for example more than ten times, of a cross-sectional area of the cryo-immersion objective 910 in a sectional direction perpendicular to the optical axis thereof. In principle the arrangement shown in FIG. 9 is also possible with an inverted cryo-immersion objective, i.e. with an upwardly pointing optical front component 40. In the same way the optical arrangement can be a reflected light and/or a transmitted light arrangement. To control the positioning, as described, mechanical components, for example guide rods, spindles and, as shown for the Z drive, a car lift kinematic system, can be used. The cooling of the immersion liquid with liquid nitrogen is also present in FIG. 9, but not shown.

Also with the variant shown in FIG. 9, it can be ensured in an excellent manner that the stative 18 can remain during microscope operation essentially at room temperature, whereas the optical front component 40 is at the temperature of the cold or cooled immersion liquid (for example at the boiling temperature of liquid nitrogen, approximately −190° C.). It can also be seen from FIG. 9 how the specimen 10 to be examined, which is positioned on a specimen lifting table 90 as a specimen carrier, can be moved with the aid of mechanical manipulation means 92, 93 away from the cryo-immersion objective 910 and fed for further examination methods.

LIST OF REFERENCE NUMERALS

10 Specimen
11 Bath with liquid nitrogen
12 Immersion liquid
13 Specimen carrier, in particular specimen table or specimen holder
14 Means for providing a cooled immersion liquid, in particular container
15 Feed line for cold nitrogen supply
16 Cold nitrogen supply
18 Stative
20 Housing
21 Closure element
22 Inlet for flushing
23 Pumping channels, attachment for vacuum pump
24 Flow channels, volume to be flushed
25 Insulating volumes, volume to be evacuated
26 Front-side closure element
27 Inner housing pipe
28 Front-side closure of the inner housing pipe
29 Pipe piece
31 Heat-insulating jacket
32 Heat bridge for cooling the front lens
40 Optical front component: front lens
41 Optical front component: front plate
42 Catadioptric optical system: first hollow mirror
43 Catadioptric optical system: second hollow mirror
44 Further optical component: lens
45 Further optical component: lens
46 Cover: closure plate (e.g. made of quartz)
47 Intermediate space between main housing 512 and separate housing 514
50 Lens
52 Piezo-actuators
53 Lens adjustable in z direction
54 Inner housing
60 Manipulation means for mechanical manipulation: drive for positioning specimen
61 Inlet for immersion liquid
62 Outlet for immersion liquid
63 Feed line for immersion liquid
64 Cooled specimen holder
70 Insulating means
71 Insulating means, heat-insulating housing portion, pipe piece made of ceramic
72 Insulating means, insulating housing made of ceramic
73 Insulating means, housing pipe made of ceramic
74 Insulating means, housing made of ceramic
80 Fixing device/fixing means
90 Specimen lifting table
91 Double arrow, degree of mobility of the specimen lifting table 90 in the vertical direction
92 Drive
93 Spindle
100 Device according to the invention
110 Cryo-immersion objective
200 Device according to the invention
210 Cryo-immersion objective
300 Device according to the invention
310 Cryo-immersion objective
400 Device according to the invention
410 Cryo-immersion objective
500 Device according to the invention
510 Cryo-immersion objective
512 Main housing
514 Separate housing
516 Separate housing
600 Device according to the invention
610 Cryo-immersion objective
700 Device according to the invention
710 Cryo-immersion objective
712 Main housing
714 Separate housing
800 Device according to the invention
810 Cryo-immersion objective
812 Main housing
814 Separate housing 900 Device according to the invention
910 Cryo-immersion objective
M Measurement position
T Transfer position

The invention claimed is:

1. A device for optical examination of a specimen, comprising:
   a cryo-immersion objective,
   a stative, to which the cryo-immersion objective is fixed,
   wherein the cryo-immersion objective has a plurality of optical components,
   wherein the cryo-immersion objective has an optical front component which is in contact during operation with a coolable immersion liquid,
   wherein at least the optical front component of the cryo-immersion objective is accommodated in or on a separate housing,
   wherein two optical front components are present on the separate housing on opposite sides, and
   wherein the other optical components of the cryo-immersion objective are accommodated in or on a main housing,
   a specimen carrier for a specimen to be examined,
   means for providing a cooled immersion liquid between the optical front component and the specimen to be examined on or against the specimen carrier, characterized in that
   insulating means are present for interrupting a heat transition between the stative and the optical front component.

2. The device according to claim 1,
characterized in that
the cryo-immersion objective has a housing and
at least a part of the insulating means is formed by a heat-insulating housing portion of the housing.

3. The device according to claim 1,
characterized in that
fixing means are present, with which the cryo-immersion objective is fixed to the stative, and
the fixing means at the same time form at least a part of the insulating means.

4. The device according to claim 1,
characterized in that
pumping channels are formed as part of the insulating means in the cryo-immersion objective to pump down an insulating volume.

5. The device according to claim 1,
characterized in that
the housing of the cryo-immersion objective is formed by an inner housing and an outer housing,
wherein a part of the insulating means is formed by an intermediate space between the inner housing and the outer housing.

6. The device according to claim 5,
characterized in that
the optical front component is held on the outer housing, and the other optical components of the cryo-immersion objective are held on the inner housing.

7. The device according to claim 5,
characterized in that
the intermediate space can be evacuated.

8. The device according to claim 1,
characterized in that
the cryo-immersion objective is surrounded at least partially by a heat-insulating jacket as part of the insulating means.

9. The device according to claim 1,
characterized in that
as part of the insulating means, an at least partial heat-insulating jacket of the separate housing is present.

10. The device according to claim 1,
characterized in that
a distance between an outer-lying optical component in the separate housing and an outer-lying optical component in the main housing is greater than 2 mm.

11. The device according to claim 1,
characterized in that
a means for flushing an intermediate space between the separate housing and the main housing with a dry gas is present.

12. The device according to claim 11,
characterized in that
the dry gas is at least one of nitrogen or dry air.

13. The device according to claim 1,
characterized in that
a volume for receiving the specimen to be examined and for receiving immersion liquid is formed in the separate housing.

14. The device according to claim 1,
characterized in that
manipulation means for mechanical manipulation of the specimen to be examined within the separate housing are present on the separate housing.

15. The device according to claim 1,
characterized in that
mechanical manipulation means for adjusting the separate housing relative to the main housing are present.

16. The device according to claim 1,
characterized in that
the optical front component and at least one further optical component of the cryo-immersion objective are arranged in or on the separate housing and
an intermediate space between the further optical component and the optical front component can be evacuated.

17. The device according to claim 1,
characterized in that
two cryo-immersion objectives are present which are orientated coaxially and counter relative to each other.

18. The device according to claim 1,
characterized in that
the optical front component is formed by at least one of a lens, a lens with a planar front side, a front plate, or a mirror of a catadioptric optical system.

19. The device according to claim 1,
characterized in that
the numerical aperture of the cryo-immersion objective is greater than 1.

20. The device according to claim 1,
characterized in that
the cryo-immersion objective has at least one optical component that is adjustable in z direction.

21. The device according to claim 1,
characterized in that
flow channels are formed in the cryo-immersion objective for flushing through with an inert gas.

22. The device according to claim 21,
characterized in that
the inert gas is at least one of dry air or nitrogen.

23. The device according to claim 1,
characterized in that
the cryo-immersion objective has a catadioptric optical system.

24. The device according to claim 1,
characterized in that
the cryo-immersion objective is sealed to prevent the penetration of immersion liquid.

25. The device according to claim 1,
characterized in that
the means for providing the cooled immersion liquid have a container for receiving the immersion liquid, wherein the cryo-immersion objective immerses at least partially into the immersion liquid during operation.

26. The device according to claim 1,
characterized in that
a cover is present for preventing the escape of evaporating immersion liquid.

27. The device according to claim 1,
characterized in that
the means for providing the immersion liquid are formed by a line for conveying immersion liquid between the optical front component and the specimen to be examined.

28. The device according to claim 1,
characterized in that
means for cooling the immersion liquid are present at temperatures below 110 K.

29. The device according to claim 28,
characterized in that
the means for cooling the immersion liquid is a bath with liquid nitrogen.

30. The device according to claim 1,
characterized in that
a distance between a first optical component and a second optical component of the microscope objective which directly follows the first component in the optical beam path of the microscope objective, is greater than 2 mm.

31. The device according to claim 1,
wherein the cryo-immersion objective has a plurality of lenses.

32. The device according to claim 1,
characterized in that
the cryo-immersion objective has a housing and
at least a part of the insulating means is formed by a pipe-piece-like heat-insulating housing portion of the housing.

33. The device according to claim 1,
characterized in that
a distance between an outer-lying optical component in the separate housing and an outer-lying optical component in the main housing is greater than 3 mm.

34. The device according to claim 1,
characterized in that
a distance between an outer-lying optical component in the separate housing and an outer-lying optical component in the main housing is greater than 4 mm.

35. The device according to claim 1,
characterized in that
two identical optical front components are present on the separate housing on opposite sides.

36. The device according to claim 1,
characterized in that
two identical cryo-immersion objectives are present which are orientated coaxially and counter relative to each other.

37. The device according to claim 1,
characterized in that
the cryo-immersion objective has at least one lens that is adjustable in z direction.

38. The device according to claim 1,
characterized in that
a distance between the optical front component and a lens of the cryo-immersion objective which directly follows the optical front first component in the optical beam path of the microscope objective, is greater than 2 mm.

39. The device according to claim 1,
characterized in that
a distance between a first optical component and a second optical component of the cryo-immersion objective which directly follows the first component in the optical beam path of the cryo-immersion objective, is greater than 3 mm.

40. The device according to claim 1,
characterized in that
a distance between a first optical component and a second optical component of the cryo-immersion objective which directly follows the first component in the optical beam path of the cryo-immersion objective, is greater than 4 mm.

41. A device for optical examination of a specimen, comprising:
a cryo-immersion objective,
a stative, to which the cryo-immersion objective is fixed,
wherein the cryo-immersion objective has a plurality of optical components, and
wherein the cryo-immersion objective has an optical front component which is in contact during operation with a coolable immersion liquid,
a specimen carrier for a specimen to be examined,
means for providing a cooled immersion liquid between the optical front component and the specimen to be examined on or against the specimen carrier,
characterized in that
insulating means are present for interrupting a heat transition between the stative and the optical front component, and
two cryo-immersion objectives are present which are orientated coaxially and counter relative to each other.

42. A method, comprising:
providing a device for optical examination of a specimen, including:
a cryo-immersion objective,
a stative, to which the cryo-immersion objective is fixed,
wherein the cryo-immersion objective has a plurality of optical components, and
wherein the cryo-immersion objective has an optical front component which is in contact during operation with a coolable immersion liquid,
a specimen carrier for a specimen to be examined,
means for providing a cooled immersion liquid between the optical front component and the specimen to be examined on or against the specimen carrier,
characterized in that
insulating means are present for interrupting a heat transition between the stative and the optical front component, and
transferring the device into an operation-ready state,
wherein the components, cooled in operation, of the cryo-immersion objective are cooled with a coolant,
wherein the immersion liquid is cooled with a coolant, and
wherein thereafter the cooled components of the cryo-immersion objective are brought into contact with an immersion liquid.

43. The method according to claim 42,
wherein the optical front component is cooled with a coolant.

44. The method according to claim 42,
wherein the components, cooled in operation, of the cryo-immersion objective are cooled with liquid nitrogen.

45. The method according to claim 42,
wherein the immersion liquid is cooled with liquid nitrogen.

46. The method according to claim 42,
wherein at least the optical front component of the cryo-immersion objective is accommodated in or on a separate housing, and
wherein the other optical components of the cryo-immersion objective are accommodated in or on a main housing.

47. The method according to claim 46, further comprising recording a plurality of microscopic images,
wherein for each of the individual images a different offset between the main housing and the separate housing is set.

* * * * *